United States Patent [19]

Dietsche

[11] 4,080,499

[45] Mar. 21, 1978

[54] SUBSTITUTED 7,8-DIHYDRO-6H-(1,2,5)THIADIAZOLO(3',4'-5,6)PYRAZINO(2,3-b)(1,4)OXAZINES

[75] Inventor: Thomas J. Dietsche, Berkeley, Calif.

[73] Assignee: The Dow Chemical Company, Midland, Mich.

[21] Appl. No.: 752,700

[22] Filed: Dec. 20, 1976

[51] Int. Cl.$^2$ ............................................ C07D 513/14
[52] U.S. Cl. ........................................ 544/101; 71/90; 424/248.51
[58] Field of Search ................................... 260/244 R

[56] References Cited

U.S. PATENT DOCUMENTS 3,850,929  11/1974  Tong ............................. 260/250 BC Primary Examiner—Henry R. Jiles
Assistant Examiner—R. W. Ramsuer
Attorney, Agent, or Firm—Gary D. Street

[57] ABSTRACT

Substituted 7,8-dihydro-6H-(1,2,5)thiadiazolo(3',4'-5,6)pyrazino(2,3-b)(1,4)oxazine compounds useful as herbicides or fungicides are disclosed.

9 Claims, No Drawings

SUBSTITUTED 7,8-DIHYDRO-6H-(1,2,5)THIADIAZOLO(3',4'-5,6)PYRAZINO(2,3-b)(1,4)OXAZINES

SUMMARY OF THE INVENTION

The present invention is directed to substituted 7,8-dihydro-6H-(1,2,5)thiadiazolo(3',4'-5,6)pyrazino(2,3-b)(1,4)oxazine compounds (hereinafter "oxazine compounds" or "oxazines") of the following formula:

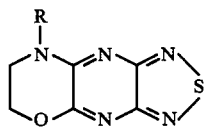

wherein, in the above formula,

R is loweralkyl of from 1 to about 6 carbon atoms, loweralkenyl of from 2 to about 4 carbon atoms or cyclohexyl.

The oxazine compounds are generally prepared by the reaction of a 5,6-dichloro-(1,2,5)thiadiazolo(3,4-b)pyrazine reactant (hereinafter "pyrazine reactant") and a mono-alkylaminoethanol (hereinafter "amine reactant") in an inert carrier solvent. The compounds of the present invention have utility as herbicides or fungicides.

DETAILED DESCRIPTION OF THE INVENTION

The reaction between the pyrazine reactant and the amine reactant to form the desired oxazine compounds of the present invention is carried out at ambient temperatures and ambient pressures. While some of the oxazine compound is formed within a few minutes, the reaction is ordinarily conducted over periods of from about 1 to about 24 or more hours to insure substantial completion of the reaction. Optionally, a catalyst, such as triethylamine, can be employed to increase the reaction rate. Following completion of the reaction, the product is recovered by filtration or where an oil is obtained, the solvent is stripped from the reaction mixture obtained and the residue treated according to conventional techniques to recover the desired product. The inert solvent carriers which can be employed include, for example, tetrahydrofuran (THF), and the like. The amine reactant is of the formula RNHCH$_2$CH$_2$OH, wherein R is as above defined, and is employed in equimolar amounts with the pyrazine reactant. An excess molar amount, usually from about a 2- to a 5-fold excess is preferably employed.

In alternative procedures, the pyrazine reactant can be reacted under reflux conditions with a similar excess amount of a dialkylaminoethanol product (R$_2$NCH$_2$CH$_2$OH wherein R is as above defined) to give a mixture comprising a bis adduct product and the desired oxazine product. The oxazine product is recovered from the reaction mixture by selective solvent extraction.

The invention is further illustrated by the following examples:

EXAMPLE 1

Methylaminoethanol (15 grams; 0.2 mol) and 10.4 grams (0.05 mol) of the pyrazine reactant (defined hereinabove) in 250 ml of tetrahydrofuran (THF) were combined and the resulting mixture stirred at room temperature for a period of about 2.5 hours. A slight exotherm was observed at initial mixing of the reactants. Following the reaction period, the reaction mixture was subjected to rotary evaporation to remove the THF. The residue thus obtained was partitioned between methylene chloride and aqueous base. The organic layer was treated with charcoal, dried over MgSO$_4$ and subjected to rotary evaporation. As a result of these operations a yellow powder was obtained and recrystallized from ethanol to give the desired 7,8-dihydro-8-methyl-6H-(1,2,5)thiadiazolo(3',4'-5,6)pyrazino(2,3-b)-(1,4)oxazine product as bright yellow crystals having a melting point of 221°–222° C.

Analysis Calcd. for C$_7$H$_7$N$_5$OS: C, 40.18; H, 3.38; N, 33.48.

Found: C, 40.13; H, 3.50; N, 33.52.

EXAMPLE 2

Diethylaminoethanol (24 grams, 0.2 mol) and 10.4 grams (0.05 mol) of the pyrazine reactant in 250 ml of THF were refluxed for a period of three hours. The reaction mixture was cooled to room temperature and the reaction mixture was then filtered to remove solid precipitate. The filtrate was subjected to rotary evaporation and the residue obtained was stirred with carbon tetrachloride. The remaining residue which did not dissolve in the carbon tetrachloride was recrystallized from isopropanol to give the desired 7,8-dihydro-8-ethyl-6H(1,2,5)thiadiazolo(3',4'-5,6)pyrazino(2,3-b)(1,4)oxazine product as a light orange solid having a melting point of 162°–163° C.

Analysis Calcd. for C$_8$H$_9$N$_5$OS: C, 43.04; H, 4.06; N, 31.37.

Found: C, 43.09; H, 4.18; N, 31.50.

EXAMPLE 3

16 grams (0.15 mol) of 2-propylaminoethanol and 10.4 grams (0.05 mol) of the pyrazine reactant in 250 ml of THF were stirred at ambient temperatures for a period of about 1 hour. The reaction mixture was then treated as in Example 1 above to obtain the desired 7,8-dihydro-8-(1-methylethyl)-6H-(1,2,5)thiadiazolo(3',4'-5,6)-pyrazino(2,3-b)(1,4)oxazine product as bright yellow needles having a melting point of 162°–163° C.

Analysis Calcd. for C$_9$H$_{11}$N$_5$OS: C, 45.55; H, 4.68; N, 29.52

Found: C, 45.61; H, 4.70; N, 30.07.

EXAMPLE 4

In a manner similar to Example 1 above, 2.0 grams (0.01 mol) of the pyrazine reactant and 4.7 grams (0.04 mol) of butylaminoethanol were reacted in 100 ml THF at ambient temperatures (overnight) to give the desired 8-butyl-7,8-dihydro-6H-(1,2,5)thiadiazolo(3',4'-5,6)-pyrazino product as yellow plates having a melting point of 89.5°–90.5° C.

Analysis Calcd. for C$_{10}$H$_{13}$N$_5$OS: C, 47.78; H, 5.22; N, 27.87

Found: C, 47.85; H, 5.13; N, 28.21.

EXAMPLE 5

A reaction mixture of cyclohexylaminoethanol (72 grams, 0.05 mol) and 10.4 grams (0.05 mol) of the pyrazine reactant and 10 grams (0.1 mol) of triethylamine in 250 ml of THF was stirred at ambient temperatures for about 2 hours and the reaction mixture then filtered and the filtrate subjected to rotary evaporation. The resulting residue was recrystallized from isopropanol and methanol to give the desired 8-cyclohexyl-7,8-dihydro-6H-(1,2,5)thiadiazolo(3',4'-5,6)pyrazino(2,3-b)(1,4)oxazine product as orange needles melting at 199°–200° C.

Analysis Calcd. for $C_{12}H_{15}N_5OS$: C, 51.98; H, 5.45; N, 25.26

Found: C, 51.96; H, 5.43; N, 25.17.

EXAMPLE 6

Allylaminoethanol (7 grams, 0.069 mol), 14 grams (0.138 mol) of triethylamine and 14.2 grams (0.069 mol) of the pyrazine reactant were reacted in 250 ml THF at room temperature for about 2 hours. The reaction mixture solution was filtered and the THF removed by rotary evaporation. The resulting brown oil residue was partitioned between methylene chloride and aqueous base, with the organic layer being separated, treated with charcoal and dried over $MgSO_4$ before being evaporated to leave a light brown solid. The solid was recrystallized from isopropanol and hexane to give the desired 7,8-dihydro-8(2-propenyl)-6H-(1,2,5)thiadiazolo(3',4'-5,6)-pyrazino(2,3-b)(1,4)oxazine product as yellow crystals having a melting point of 177°–179° C.

Analysis Calcd. for $C_9H_9N_5OS$: C, 45.95; H, 3.86; N, 29.77

Found: C, 46.05; H, 3.92; N, 29.93.

In a manner similar to the foregoing examples, other oxazine products within the scope of the present invention are similarly obtained utilizing the appropriate amine reactant.

The oxazine products of the present invention are suitable for use as herbicides or fungicides. For such uses, the unmodified substance can be utilized. However, the present invention also embraces the use of compounds in a formulation. Thus, for example, a compound can be dispersed on a finely divided solid and employed therein as a dust. Also, the compounds, or a solid composition comprising the compound, can be dispersed in water, typically with the aid of a wetting agent, and the resulting aqueous suspension employed as a spray. In other procedures, the compound can be employed as a constituent of organic liquid compositions, oil-in-water and water-in-oil emulsions, or water dispersions, with or without the addition of wetting, dispersing, or emulsifying agents.

It is to be understood, however, that all of the compounds claimed and compositions containing them may not be equally effective at similar concentrations or against the same plants or organisms. The exact concentration of the toxic substituent to be employed in the treating compositions is not critical and may vary considerably provided the plant or organism and/or their respective habitats are contacted with an effective amount of the toxicant.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides, fungicides, herbicides and nematocides.

In representative operations, each of the oxazine compounds from Examples 3 and 6 were found to give substantially complete control of pigweeds when plants of the same are sprayed to run-off with compositions containing one of said oxazine compounds at a concentration of 4000 parts per million.

In other operations, the oxazines of Examples 4 and 5 were found to give substantially complete control of crabgrass seeds when contacted at a rate of 10 lbs. per acre with compositions containing one of the oxazine compounds. In other similar operations, the growth of pigweed seeds was found to be completed inhibited when contacted with the oxazine of Example 1 at a rate of 10 pounds per acre.

In further operations, the oxazines of Examples 2, 3, 4 and 5 were found to give substantially complete control of Trichophyton mentagrophytes when such organisms are contacted with compositions containing one of the oxazine compounds at a concentration of 500 parts per million.

Other oxazines of the present invention are similarly found to have herbicide or fungicide utility.

While this invention has been described with reference to certain specific embodiments, it is of course to be understood that the invention is not to be so limited except insofar as appear in the following claims.

I claim:

1. A compound corresponding to the formula:

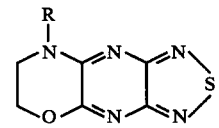

wherein, in the above formula,
R is loweralkyl of from 1 to about 6 carbon atoms, loweralkenyl of from 2 to about 4 carbon atoms or cyclohexyl.

2. The compound of claim 1 wherein R is loweralkyl.
3. The compound of claim 1 wherein R is loweralkenyl.
4. The compound of claim 1 wherein R is cyclohexyl.
5. The compound of claim 2 wherein R is methyl.
6. The compound of claim 2 wherein R is ethyl.
7. The compound of claim 2 wherein R is isopropyl.
8. The compound of claim 2 wherein R is butyl.
9. The compound of claim 3 wherein R is 2-propenyl.

* * * * *